(12) United States Patent
Hyon

(10) Patent No.: US 6,232,384 B1
(45) Date of Patent: May 15, 2001

(54) BONE FIXATION MATERIALS AND METHODS FOR THEIR PREPARATION

(75) Inventor: Suong-Hyu Hyon, Kyoto (JP)

(73) Assignee: BMG Inc., Kyoto (JP)

( * ) Notice: Subject to any disclaimer, the term of this patent is extended or adjusted under 35 U.S.C. 154(b) by 0 days.

(21) Appl. No.: 09/154,101

(22) Filed: Sep. 16, 1998

(30) Foreign Application Priority Data

Jan. 27, 1998 (JP) .................................................. 10-052638

(51) Int. Cl.$^7$ ....................................................... C08K 3/10
(52) U.S. Cl. ........................ 524/413; 524/415; 525/415; 525/450
(58) Field of Search .................... 525/450, 415; 524/413, 414

(56) References Cited

U.S. PATENT DOCUMENTS

| | | | | |
|---|---|---|---|---|
| 4,539,981 | * | 9/1985 | Tunc | 128/92 B |
| 4,550,449 | * | 11/1985 | Tunc | 128/92 C |
| 4,655,777 | * | 4/1987 | Dunn et al. | 623/16 |
| 4,781,183 | * | 11/1988 | Casey et al. | 128/92 YP |
| 5,080,665 | * | 1/1992 | Jarrett et al. | 606/219 |
| 5,108,755 | * | 4/1992 | Daniels et al. | 424/426 |
| 5,134,031 | * | 7/1992 | Kagechi et al. | 428/373 |
| 5,458,653 | * | 10/1995 | Davidson | 623/23 |
| 5,686,540 | * | 11/1997 | Kakizawa | 525/444 |

FOREIGN PATENT DOCUMENTS

| | | | |
|---|---|---|---|
| 0933089 | * | 4/1999 | (EP) . |
| WO90/07304 | * | 12/1990 | (WO) . |

* cited by examiner

*Primary Examiner*—Margaret Medley
(74) *Attorney, Agent, or Firm*—Jordan and Hamburg LLP

(57) ABSTRACT

A bone fixation material has an initial bending strength at break of more than 250 MPa, maintains its strength more than 3 months in a living body organism and has the characteristic of biodegrading and bioabsorbing into and disappearing from the organism within a range of 6 months to 3 years. The material comprises a polymer with the characteristic of biodegrading and bioabsorbing into the living body organism, a hydroxyapatite and an alkaline inorganic compound.

9 Claims, No Drawings

BONE FIXATION MATERIALS AND METHODS FOR THEIR PREPARATION

BACKGROUND OF THE INVENTION

1. Field of the Invention

The present invention relates to bone fixation material easily biodegrading and bioabsorbing into the living body organism and methods for preparing the materials. More particularly, the present invention relates to bone fixation materials for bone medical treatment use in plastic surgery, oral surgery, thoracic surgery and in addition animal bone treatment and methods for preparing these materials.

2. Description of the Related Art

Artificial biomaterials having a high bending strength are employed in order to redress bone fractures or support chests for fractured bone treatment in plastic surgery, oral surgery, and thoracic surgery. It is necessary that the bone fixation materials such as plates and screws are applied in the period that the bone is redressing and are removed as soon as possible after healing in order to prevent the bone from weakening.

Nowadays, although the bone fixation materials in clinical use are almost all composed of metals or ceramics, there are problems in which materials cause the bone to degrade, because they have too high of a level modulus, or happen to biodegrade or the metal ions are possibly dissolved into the bone. If materials having similar modulus to the bone, and which biodegrade and bioabsorb into a living organism, are employed in order to redress the bone fracture, various ill effects on the redressing of the bone will disappear because no alien substances take place in the living body over a long time.

According to the above conception and expectations, lactic acid polymers which have the characteristic of biodegrading and bioabsorbing into the living body organism are gradually being employed right now as bone fixation materials in clinical application use. It has been well-known for many years that the lactic acid polymers could be employed as bone fixation materials. For example, Japanese applied patent 59-97654 discloses a method to synthesize a lactic acid polymer, but fails to disclose a lactic acid polymer composite having a high level modulus and high level bending strength.

Japanese patent 3-63901 discloses molding conditions in which a lactic acid polymer composite contains hydroxyapatite and has the characteristic of biodegrading and bioabsorbing into the living body organism improved by uniaxial extension, mechanical properties such as modulus and bending strength useful for bone fixation materials. PCT patent WO/05312 discloses other molding conditions similar to said patent, in which a lactic acid polymer rod was uniaxially extended to a relative high draw ratio (7 to 12 times) at a relatively high temperature and attained a high level bending strength, and a high level modulus by fibrillation. Japan applied patent 1-198553 discloses bone cementing materials, of which lactic acid polymer was composed of a viscosity-average molecular weight of more than 200,000 after molding and uniaxial extension. Furthermore, Japanese applied patent 9-135892 also discloses molding conditions, in which molecules were oriented parallel not to the main, but to the plural axes during molding in order to reduce anisotropy of the bending strengths in a composite.

However, the patents mentioned above only concern initial bending strength and the hydrolyzing durability of bone fixation materials and fail to disclose its bending strength in a living body organism and its durability. There is not enough description concerning biodegradation and bioabsorption into the living body organism after redressing, and especially no description of the method to promote biodegradation and the bioabsorption after the bending strength has left. It takes only about 6 to 8 months to perfectly redress a bone fracture. However, the bending strength of the bone connecting materials characteristically biodegrade and bioabsorb, gradually decreasing after embedding into the body in accordance with the decrease of the molecular weight, and decrease to 0 within 4 months. The molecular weight of the materials reduces from about 200,000 at first to several thousands, to several tens of thousands, while a lot of granular crystallite still remains for 3 to 5 years (J. E. Bergsma et al. Biomaterials, 16(4), 267–274,1995). As a result, when the bone connecting materials mentioned above are employed for a material to redress bone fractures, it takes, for example, from 3 to 5 years for the fibrous tissues to perfectly retrieve bone tissue, because the velocity of biodegradation and bioabsorption is too slow. In addition, recreated bones can not invade into and embed with parts of the bone connecting materials even after healing and, therefore, vomicae in the bone remains almost forever. It causes a reduction in mechanical tenacity which bears a load at first. Added to the above problem, many serious late complications can occur after healing (J. E. Bergsma et al. Biomaterials, 16(1), 25–32,1995).

SUMMARY OF THE INVENTION

The present invention proposes a bone fixation material having an initial bending strength at break of more than 250 MPa, maintaining this strength for more than 3 months in a living body organism after which it characteristically biodegrades and bioabsorbs into the organism and disappears within a range of 6 months to 3 years. It is preferred that the material includes a polymer which characteristically biodegrades and bioabsorbs into the living body organism, a hydroxyapatite and an alkaline inorganic compound. It is highly preferred that the chain molecules of the polymer are extended and oriented parallel to the major axis or plural axes, and, it is preferred that the polymer be a lactic acid polymer composed of a L type and D, L type mixture or copolymer of 70 to 100% in a mole percentage of the L type, or a copolymer of a lactide and a glycolide. It is also highly preferred that the composite ratio of the polymer and the hydroxyapatite is in a weight ratio range of 99:1 to 60:40, and the composite ratio of the hydroxyapatite and the alkaline inorganic compound is in a weight percentage range of 99.9:0.01 to 80:20.

Furthermore, the present invention proposes a method of making a bone fixation material which includes: (A) providing a melt which has the characteristic to biodegrade and bioabsorb into the living body organism in itself, and which comprises a polymer with the characteristic of biodegrading and bioabsorbing into the living body organism, a hydroxyapatite and an alkaline inorganic compound, (B) molecularly orienting the melt by applying it, at an extendible and moldable temperature, to a process of extension or molding selected from the group consisting of a uniaxial extension, an extruding extension, a milling and compression molding, and (C) extending chain molecules of the polymer and orienting them parallel to the major axis or plural axes. It is preferred that the extension is a ram extrusion at high pressure or a hydrostatic extrusion at a temperature range of 80 to 160° C.

DETAILED DESCRIPTION OF THE INVENTION

The bone fixation material of the present invention includes a polymer with the characteristic of biodegrading and bioabsorbing into the living body organism, a hydroxyapatite and an alkaline inorganic compound. The polymer is a lactic acid polymer, preferably a L type lactic acid polymer having more than 95% optical purity. However, it is highly preferable that it is in an optical purity range of 80 to 95%, to prevent the polymer from having too high crystallinity. Of course, the crystallinity relates to the initial modulus and bending strength at break and a bone fixation material having high tenacity and modulus is easily composed from a high crystallinity polymer. However, as objective tenacity and modulus are possibly derived from the orientation of the molecular chain in a crystalline state during molding, the crystallinity is preferably lowered in order to better bioabsorb it into and eliminate it from the organism as soon as possible after biodegradation. It is highly preferred in the present invention that the polymer, as a raw material, is a lactic acid polymer composed of a L type and D,L type mixture of 85 to 95% in a mole percentage of the L type, a copolymer of a lactide and a glycolide. The polymer is preferably composed of viscosity-average molecular weight of more than 80,000, and more preferably in a range of 100,000 to 500,000

The hydroxyapatite, a cow bone powder or its mixture instead of a pure hydroxyapatite, is preferably employed in the present invention. Because the cow bone powder also shows alkalinity, it is preferred that the hydroxyapatite is alkalized by an alkaline inorganic compound beforehand. Furthermore, the hydroxyapatite can possibly be fabricated by the method in which a ceramic is heated and mixed by a supersonic or hyper-sermere and decomposed by heating.

The alkaline inorganic compound may be, for example, a hydroxide group, the compound being, for example, potassium hydroxide, calcium hydroxide or magnesium hydroxide; a chloride group, the compound being, for example, potassium chloride, calcium chloride, magnesium chloride or zinc chloride. Alternatively, the compound may be an alkali metal salt or a basic organic compound such as an amine. The compound is adhered to a hydroxyapatite surface. A chloride compound such as calcium chloride can possibly be employed in spite of its original neutrality because the chloride compounds sold in the market contain several percentage points of calcium hydroxides and their chloride solutions exhibit strong alkalinity.

The composite ratio of the polymer and the hydroxyapatite is preferably in a weight ratio range of 99:1 to 60:40, and more preferably 80:20 to 70:30. The composite ratio of the hydroxyapatite and the alkaline inorganic compound is preferably in a weight percentage range of 99.9:0.01 to 80:20, and more preferably 95:5 to 90:10. It is preferred that the alkali inorganic compound is mixed with the hyroxyapatite, or that the hydroxyapatite is dipped in the alkali inorganic compound solution in order to coat the hydroxyapatite surface.

A composite of a lactic acid polymer with the characteristic of biodegrading and bioabsorbing into the living body organism, a copolymer of a lactide and a glycolide having more than 100,000 molecular weight, and a hydroxyapatite having an excellent bone affinity, is employed as a bone fixation material and is uniaxially extended in order to maintain bending strength at break of more than 250 MPa for a period of more than 3 months until the bone fracture is redressed in the organism. However, the bone fixation material mentioned above certainly improves the initial bending strength and hydrolyzing durability, but it does not improve the maintenance of the bending strength in a living body organism and its durability while it is embedded into the body. Therefore, the materials can not completely disappear from the organism and the bending strength can not decrease to 0 in 4 months.

The present invention concerns making the material biodegrade and bioabsorb into the living body organism as soon as possible after the bending strength decreases to 0. It is based on the knowledge that the lactic acid polymer with a characteristic of biodegrading and bioabsorbing into the organism is a kind of fatty acid ester, and is hydrolyzed by a non-fermentation reaction in the living organism and this hydrolyzing velocity is low in an acid state and high in an alkali state (Gen et al. Degradation of high molecular weight poly L-lactide in alkaline medium, Biomaterials, 16, 833–843, 1995). Although the lactic acid polymer composite shows almost no molecular weight decrease caused by hydrolysis in the organism within 4 months, after 4 months water molecules deeply invade into the organism and the composite shows a large molecular decrease as a whole owing to hydrolysis. In an ordinary case, the hydrolysis in the organism takes place as follows:

1. When a partial pH changes to acid state in the accordance with hydrolysis,
2. The rate of molecular weight decrease changes slowly,
3. And prior hydrolysis occurs in an amorphous area at the same time,
4. Crystallite, having a relatively low molecular weight (1,000 to 10,000), remains in the bone organism, and
5. The hydrolyzing velocity slows further.

In the present invention, it is possible that when water molecules invade the bone of the organism after about 4 months, the hydrolyzing velocity increases and the material is then biodegraded and disappears from the organism owing to the increase in the bone's pH to an alkali state (pH of more than 7).

The method of making a bone fixation material in the present invention is as follows:

(A) providing a melt having a characteristic to biodegrade and bioabsorb into the living body organism fabricated from a polymer with the characteristic of biodegrading and bioabsorbing into the living body organism, a hydroxyapatite and an alkaline inorganic compound;

(B) applying the melt in a desirable shape, such as a rod or sheet, by means for molecularly orienting selected from the group consisting of a uniaxial extension, an extension extrusion, a milling and compression molding, at an extendible and moldable temperature; and (C) extending and orienting the melt composite parallel to the major axis or to plural axes.

A ram extrusion at a high pressure or a hydrostatic extrusion are preferably employed as the extension means in order to create a material having an initial bending strength of more than 250 Mpa. The temperature, as stated above, is preferably in a range of a glass transition temperature (about 60° C.) to a melting temperature (about 180° C.) of the lactic acid polymer, more preferably in a range of 80 to 140° C.

In conclusion, the bone fixation material in the present invention, which has the characteristic of biodegrading and bioabsorbing into the living body organism, is a material having both initial high bending strength and a promotion effect of biodegradation and bioabsorption after 6 months, and, therefore, it is nearly an ideal one. The advantages of the invention cannot be obtained using a known bone fixation material which is composed of a lactic acid polymer.

The bone fixation materials in the present invention are useful for bone medical treatment use in plastic surgery, oral surgery, thoracic surgery and animal bone treatment involving shaped objects, including plates and screws. It works in the period it takes for the bone to redress and is removed as soon as possible after healing in order to prevent the bone from weakening.

EXAMPLES

These Examples give a detailed explanation, but do not restrict the scope of the present invention. The compressed bending strengths and modulus mentioned in the Examples are estimated in accordance with the three-point bending test described in JIS-K.

Examples 1 to 6

An L lactic acid polymer, and a copolymer of L lactide and L, D lactide were synthesized from respective raw materials sold in the market as a polymerization initiator of tin octylate by ring opening polymerization under reduced pressure. The copolymer composite ratios of L lactide and L,D lactide were 100:0 and 85:15. Viscosity average molecular weights of said polymer and copolymer were about 360,000, respectively. The alkalized hydroxyapatite was fabricated by dipping hydroxyapatite (HA) powder (calcined at 1200° C., to 5.5 um average particle diameter) in a 30% calcium hydroxide solution and drying. Molded columns of about 10 mm were fabricated by the method, in which a mixture of the above 2 polymers and the alkalized hydroxyapatite powder at a mixture ratio of 70:30 by weight percentage was dried a day and night at a relatively high temperature (120 to 130° C.) under reduced pressure and extruded at about 200° C. The columns were extended 3 times at 120° C. in liquid paraffin and deformed to about one-fifth of the original size by hot pressing at 140° C. Furthermore, the column was extended to 3× extended magnification in a glycerin bath by a hydrostatic extrusion.

The bending strengths of the molded column are shown in Table 1.

Comparative Examples 1 to 6

A copolymer of L lactide and L,D lactide was synthesized as 85:15 of a copolymer composite ratio of L lactide and L,D lactide similar to Example 1. Three kinds of molded columns were fabricated without the alkalized hydroxyapatite, similarly to the method mentioned in Example 1.

The bending strengths of the molded columns are shown in Table 2.

Examples 7 to 12

The molded column fabricated in the above Examples 1 to 6 was dipped in a 10 ml physiological solution and weight variations of the molded column were observed after hydrolyzing a long time (about 1 to 2 years) at 37° C.

The weight variations are shown in Table 3.

Comparative Examples 7 to 12

The molded column fabricated in the above Comparative Examples 1 to 6 was dipped in a 10 ml physiological solution and weight variations of the molded column were observed after hydrolyzing a long time (about 1 to 2 years) at 37° C., similarly to Examples 7 to 12.

The weight variations are shown in Table 4.

As shown in Table 1, the bone fixation materials with the characteristic of biodegrading and bioabsorbing into a living body organism, mentioned in Examples 1 to 6 of the present invention, have bending strengths of more than 250 MPa after applying molecularly orientated means selected from the group consisting of a uniaxial extension, an extension extrusion, a milling and compression molding to a mixture composed of an alkalized hydroxyapatite and a polymer with the characteristic of biodegrading and bioabsorbing into the organism. In addition, as shown in Table 3 of Examples 7 to 12, residual material has completely disappeared from the organism and the weight of the material is reduced to 0 within 2 years from the beginning of the hydrolyzing experiment. As a result, the molded composite is shown to be easily decomposed by the effect of the alkalized hyroxyapatite. On the other hand, as shown in Table 4 of Comparative Examples 7 to 12, if a molded column contains no alkalized hydroxyapatite, residual material of more than 30% remains in the organism even after 2 years of beginning the hydrolyzing experiment, and the biodegradation velocity looked very slow. The difference looks clear between both these Examples and the Comparative examples.

TABLE 1

| | Polymer (%) | | Alkalized Hydroxy-apatite (wt. %) | Initial Bending Strength (MPa) |
|---|---|---|---|---|
| | PLLA 100% | P(L-LA-co-DL-LA) 85/15% | | |
| Example 1 Uniaxial Extension (×3) | 100 | 0 | 30 | 280 |
| Example 2 Compression Molding (×⅕) | 100 | 0 | 30 | 310 |
| Example 3 Hydrostatic Extrusion (×3) | 100 | 0 | 30 | 370 |
| Example 4 Uniaxial Extension (×3) | 0 | 100 | 30 | 250 |
| Example 5 Compression Molding (×⅕) | 0 | 100 | 30 | 255 |
| Example 6 Hydrostatic Extrusion (×3) | 0 | 100 | 30 | 330 |

TABLE 2

| | Polymer (%) | | Alkalized Hydroxy-apatite (wt. %) | Initial Bending Strength (MPa) |
|---|---|---|---|---|
| | PLLA 100% | P(L-LA-co-DL-LA) 85/15% | | |
| Comparative Example 1 Uniaxial Extension (×3) | 100 | 0 | 0 | 220 |
| Comparative Example 2 Compression Molding (×⅕) | 100 | 0 | 0 | 240 |
| Comparative Example 3 Hydrostatic Extrusion (×3) | 100 | 0 | 0 | 280 |

TABLE 2-continued

|  | Polymer (%) | | Alkalized Hydroxy-apatite (wt. %) | Initial Bending Strength (MPa) |
|---|---|---|---|---|
|  | PLLA 100% | P(L-LA-co-DL-LA) 85/15% | | |
| Comparative Example 4 Uniaxial Extension (×3) | 0 | 100 | 0 | 210 |
| Comparative Example 5 Compression Molding (×⅕) | 0 | 100 | 0 | 220 |
| Comparative Example 6 Hydrostatic Extrusion (×3) | 0 | 100 | 0 | 250 |

TABLE 3

|  | Polymer (%) | | Alkalized Hydroxy-apatite (wt. %) | Residual Material (%) | |
|---|---|---|---|---|---|
|  | PLLA 100% | P(L-LA-co-DL-LA) 85/15% | | After 1 Year | After 2 Years |
| Example 7 Uniaxial Extension (×3) | 100 | 0 | 30 | 23 | 0 |
| Example 8 Compression Molding (×⅕) | 100 | 0 | 30 | 27 | 0 |
| Example 9 Hydrostatic Extrusion (×3) | 100 | 0 | 30 | 31 | 0 |
| Example 10 Uniaxial Extension (×3) | 0 | 100 | 30 | 0 | 0 |
| Example 11 Compression Molding (×⅕) | 0 | 100 | 30 | 0 | 0 |
| Example 12 Hydrostatic Extrusion (×3) | 0 | 100 | 30 | 0 | 0 |

TABLE 4

|  | Polymer (%) | | Alkalized Hydroxy-apatite (wt. %) | Residual Material (%) | |
|---|---|---|---|---|---|
|  | PLLA 100% | P(L-LA-co-DL-LA) 85/15% | | After 1 Year | After 2 Years |
| Comparative Example 7 Uniaxial Extension (×3) | 100 | 0 | 0 | 62 | 32 |
| Comparative Example 8 Compression Molding (×⅕) | 100 | 0 | 0 | 65 | 37 |
| Comparative Example 9 Hydrostatic Extrusion (×3) | 100 | 0 | 0 | 73 | 45 |
| Comparative Example 10 Uniaxial Extension (×3) | 0 | 100 | 0 | 48 | 30 |
| Comparative Example 11 Compression Molding (×⅕) | 0 | 100 | 0 | 57 | 30 |
| Comparative Example 12 Hydrostatic Extrusion (×3) | 0 | 100 | 0 | 59 | 31 |

What I claim is:

1. A bone fixation material having an initial bending strength at break of more than 250 MPa, having the property of maintaining its strength for more than 3 months in a living body organism, and having the caacteristic of biodegrading and bioabsorbing into and disappearing from the organism within a range of 6 months to 3 years, said material comprising a L and/or D lactic acid polymer or copolymer having the characteristic of biodegrading and bioabsorbing into the living body organism, a hydroxy apatite, and an alkaline inorganic compound or basic organic compound capable of raising the pH of the composition to an alkaline state in the presence of water, wherein the composite ratio of the polymer and the hydroxyapatite is in weight ratio range of 99:1 to 60:40 and the ratio of the hydroxyapatite and the alkaline inorganic compound is in a weight percent range of 99.9:0.01 to 80:20.

2. A bone fixation material, according to claim 1, wherein chain molecules of the polymer are extended and oriented parallel to the major axis or plural axes.

3. A bone fixation material, according to claim 1, wherein the polymer is a L-lactic acid polymer or a L-lactic acid polymer and D, L lactic acid polymer mixture of 70 to 100% in a mole percentage of L lactic acid polymer.

4. A bone fixation material, according to claim 1, wherein the polymer is a copolymer of a lactide and a glycolide.

5. A bone fixation material, according to claim 1, wherein the composite ratio of the polymer and the hydroxyapatite is in a weight ratio range of 80:20 to 70:30.

6. A bone fixation material, according to claim 4, wherein the composite ratio of the hydroxyapatite and the alkaline inorganic compound is in a weight percentage of 95:5 to 90:10.

7. A bone fixation material according to claim 1, wherein the hydroxyapatite is cow bone powder.

8. A bone fixation material according to claim 1, wherein the alkaline inorganic compound is selected from compounds containing a hydroxide group, a chloride group, or is an alkali metal salt.

9. A bone fixation material according to claim 8, wherein the compounds containing the hydroxide group are selected from potassium hydroxide, calcium hydroxide or magnesium hydroxide; the compounds containing the chloride group are selected from potassium chloride, calcium chloride, magnesium chloride or zinc chloride; and the basic organic compound is an amine, said compounds containing the chloride group also containing sufficient hydroxide to import alkalinity to the compound.

* * * * *